(12) United States Patent
Barfuss et al.

(10) Patent No.: US 7,369,694 B2
(45) Date of Patent: May 6, 2008

(54) METHOD AND MEDICAL DEVICE FOR THE AUTOMATIC DETERMINATION OF COORDINATES OF IMAGES OF MARKS IN A VOLUME DATASET

(75) Inventors: Helmut Barfuss, Erlangen (DE); Karl Barth, Hoechstadt (DE); Gerd Wessels, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 729 days.

(21) Appl. No.: 10/722,225

(22) Filed: Nov. 25, 2003

(65) Prior Publication Data

US 2005/0018891 A1    Jan. 27, 2005

(30) Foreign Application Priority Data

Nov. 25, 2002 (DE) ................................ 102 54 942

(51) Int. Cl.
*G06K 9/00* (2006.01)
(52) U.S. Cl. ...................... 382/131; 382/154; 382/173; 382/285; 382/287
(58) Field of Classification Search ..................... None
See application file for complete search history.

(56) References Cited

U.S. PATENT DOCUMENTS 5,769,789 A    6/1998  Wang et al.
5,799,099 A    8/1998  Wang et al.
6,052,477 A *  4/2000  Wang et al. ................ 382/131

FOREIGN PATENT DOCUMENTS

DE    44 35 796    12/1996
DE    199 51 502    1/2001
WO    WO 02/43007    5/2002

OTHER PUBLICATIONS

"Digital Picture Processing," Rosenfeld et al (1982), pp. 37-49.*
"Volume Registration by Surface Point Signature and Mutual Information Maximization with Applications in Intra-Operative MRI Surgeries," Eldeib et al, Proc. Int. Conf. On Image Processing, vol. 1 (2000) 200-203.*

(Continued)

*Primary Examiner*—Jingge Wu
*Assistant Examiner*—Sean Motsinger
(74) *Attorney, Agent, or Firm*—Schiff Hardin LLP

(57) ABSTRACT

In a method and medical device for determining the coordinates of images of marks in a volume dataset, the marks are disposed on the surface of a subject, and the volume dataset represents the images of the marks and an image of at least the part of the subject on whose surface the marks are disposed. A data processing system stores the volume dataset. The volume dataset is picked up by a first imaging medical device and represents an image of at least a part of the subject on whose surface several marks disposed and images of the marks. With a navigation system, a relation of the coordinates of the volume dataset to the coordinates of the subject is provided in the form of a coordinate transformation during a registration.

13 Claims, 6 Drawing Sheets

OTHER PUBLICATIONS

"International Organizations For Standardization, Standards of JTC 1/SC 31".

"Volume Registration by Surface Point Signature and Mutual Information Maximization with Applications in Intra-Operative MRI Surgeries," Eldev et al, Proc. Int. Conf. On Image Processing, vol. 1 (2000) pp. 200-203.

"Image Processing and Display of 3D of Intra-Coronary Ultrasound Images," Herrington et al, Proc. Computers in Cardiology (1991) pp. 349-352.

* cited by examiner

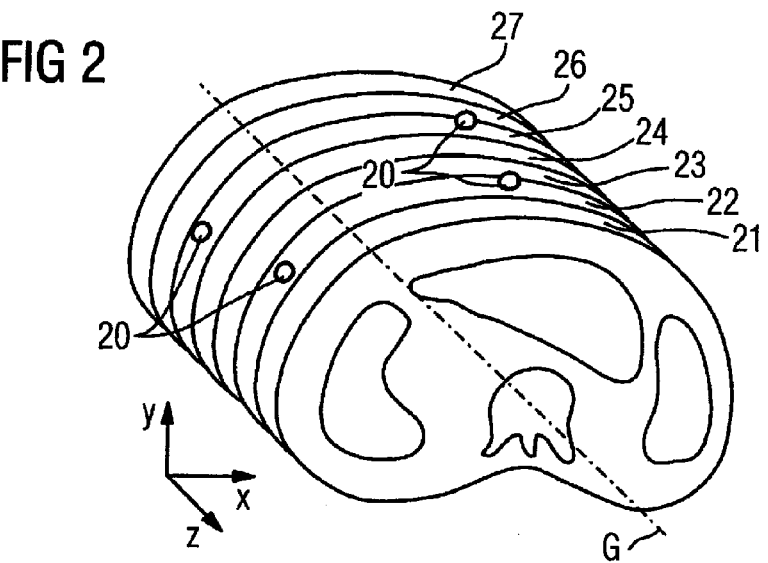
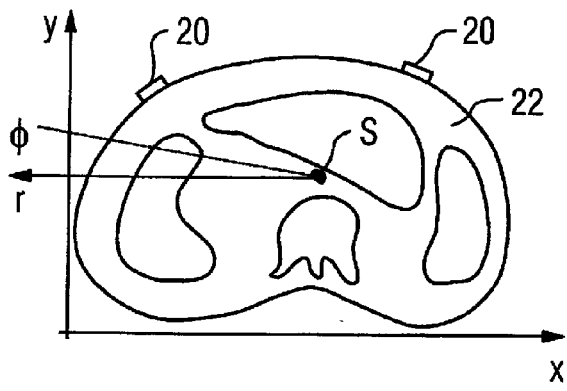
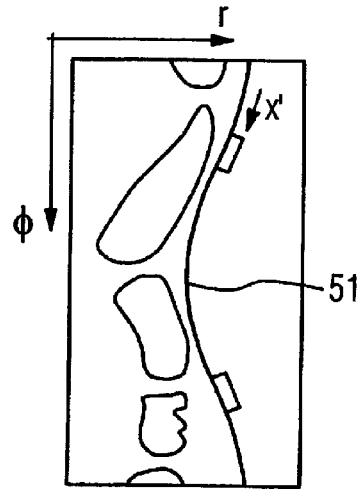

METHOD AND MEDICAL DEVICE FOR THE AUTOMATIC DETERMINATION OF COORDINATES OF IMAGES OF MARKS IN A VOLUME DATASET

BACKGROUND OF THE INVENTION

1. Field of the Invention

The present invention relates to a method for computing the coordinates of images of marks in a volume dataset, the coordinates referencing the actual position and orientation coordinates of a physical object or living being. The invention further relates to a medical device with a data processing device for storing a volume dataset and a navigation system.

2. Description of the Prior Art

A method and medical device of the above type are needed in the navigation of a medical instrument or in image fusion. An example of navigation of a medical instrument is described in German OS 199 51 502. A volume dataset of the body region of interest of a patient is generated by means of a computed tomography device. During a minimally invasive intervention, in particular, a surgeon guides the medical instrument into the body of the patient. A position sensor of the navigation system is disposed at the medical instrument, so that the navigation system determines the position, i.e. the location and orientation, of the medical instrument relative to the patient's body. Based on the position determination, the determination of the location coordinates of the medical instrument, an image of the medical instrument can then be merged into the image that is allocated to the volume dataset, which is displayed on a monitor.

The volume dataset can be produced preoperatively, e.g. with a computed tomography apparatus. Fading in the image of the medical instrument requires a spatial transformation of the coordinates of the position sensor of the navigation system, which is disposed at the medical instrument in a defined manner, the coordinates referencing a first coordinate system, into the spatial coordinates of the image of the patient that is acquired with the computed tomography apparatus and utilized for the navigation. This transformation is referred to as registration.

Marks are made on the patient, usually on the body surface, for registration. Locations in the environment of the operation area that move as little as possible are selected. The marks remain fixed on the patient during the entire image supported procedure. i.e. both during the recording of the volume dataset and during the intervention. The contrast of the marks can be relatively weak, because they are frequently relatively small for reasons of space. Furthermore, relatively weakly contrasting marks are used so that the remaining image volume is impaired as little as possible by artifacts. Given the quality of modern computed tomography or magnetic resonance devices, it is usually no problem to tap these marks manually, for instance in two orthogonal views, in order to determine their spatial positions. This technique is relatively time-consuming, because it is usually necessary to sift through almost the entire volume dataset in order to find the images of the marks in the volume dataset. Moreover, at least three images of marks must be captured.

In U.S. Pat. Nos. 5,769,789, 5,799,099 and 6,052,477, a method is described in which the search, for instance for MR and CT head shots, is performed automatically. The entire volume dataset is examined during the search. Substantially morphological operators are applied, which correspond to the mark dimensions, and a threshold separation is performed. This procedure is relatively calculation-intensive. Furthermore, the application of the filter operations to the entire volume dataset raises the probability of falsely recognized images of marks. The method is also limited in the specificity of the operators, because markers are oriented randomly in space.

Each image of a mark that is identified in the volume dataset must be tapped on the patient with the position sensor of the navigation system for the actual registration. This produces the relation of the coordinates of the volume dataset to the coordinate system of the navigation system. A corresponding transformation matrix is calculated from the coordinates of the marks and the coordinates of the images of the marks in the volume dataset, and the registration is terminated.

Another application in which the coordinates of images in a volume dataset are needed is when a corresponding CT view is needed, particularly for a current endoscopic, laparoscopic, or ultrasound image, in order to superimpose the two views.

SUMMARY OF THE INVENTION

It is thus an object of the invention to provide a method that allows the calculation, with a reduced computing expenditure and with increased reliability, of the coordinates of the images of marks on a subject, for instance a living being, the images being stored in a volume dataset. Another object of the invention is to allow the calculation of images of marks in a volume dataset with a reduced computing expenditure by constructing a medical device with a date processing device for storing a volume dataset and with a navigation system, with the volume dataset, that represents an image of a body of a subject at whose surface several marks are arranged, and images of these marks—is recorded with a first imaging medical device, and the coordinates of the volume dataset are related to the coordinates of the subject by means of a coordinate transformation with the navigation system during a registration.

The object of the invention is achieved by a method for determining the coordinates of images of marks in a volume dataset, wherein the marks are disposed on the surface of a subject, and the volume dataset contains the images of the marks and an image of at least the part of the subject on whose surface the marks are disposed, including the following steps of segmenting of the image of the surface, transform the volume dataset such that the segmented image of the surface is transformed into a plane, generate an image dataset substantially containing the pixels of the image of the surface that was transformed into the plane as well as pixels of the images of the marks, determining the coordinates of the images of the marks in the image dataset, and determining the coordinates of the images of the marks in the volume dataset.

As mentioned above, even with modern computers it is relatively time-consuming to search through a volume dataset for images of marks that are recorded in the volume dataset, particularly because the marks can be randomly oriented on the surface of the subject. The subject is a technical object or a living being. The inventive method reduces the dimension of the original three-dimensional search process. According to the inventive method, the surface of the subject, which is imaged in the volume dataset, is first calculated (segmented out) automatically. When the subject is a living being, in particular, the image of the surface, i.e. the body surface of the living being, represents a curved surface.

Next in accordance with the invention, the volume dataset is transformed in such a way that the segmented image of the surface of the subject is transformed into the plane, as if the image of the subject were to be unrolled. The projection of the surface of the earth is an analogy. A few millimeters above and below the image of the surface are calculated into the unrolled flat view of the image of the surface, in order to obtain the image data that contain the images of the marks on the surface. The next image dataset is then acquired, containing the image of the surface subsequent to its being unrolled into the plane (transformed) and the images of the marks. In this image dataset, the coordinates of the images of the marks are then calculated. Because the resulting image dataset is substantially smaller than the original volume dataset and, above all, because it is guaranteed that all the marks lie in the same (parallel) orientation in one plane, the calculation of the coordinates of the images of the marks in the image dataset is less intensive than the direct calculation of the coordinates of the images in the volume dataset. The 3D pattern recognition and search problem in the volume dataset are reduced, namely to a 2D task, by the described transformation into the planar image dataset.

The object of the invention also is achieved by a method for calculating the coordinates of images of marks in a volume dataset that is present in the form of several consecutive computed tomography slice images and in which the image data of each slice image are described with Cartesian coordinates, wherein the marks are disposed on the surface of a subject, and the volume dataset contains the images of the marks and an image of at least the part of the subject at whose surface the marks are disposed, including the steps of performing a coordinate transformation for each slice image to polar coordinates relative to a line extending through the image of the subject which is oriented at least substantially perpendicular to the individual slice images, determining the contours that are imaged in each transformed slice image and allocated to the image of the surface, generating an image dataset substantially contains the pixels of the image of the surface after its transformation into the plane, and pixels of the images of the marks, generating a two-dimensional image dataset by re-extracting image data representing the images of the marks in a region parallel to the imaged surface that has been calculated, determining coordinates of the images of the marks in the two-dimensional image dataset; and retransforming the coordinates of the images of the marks back into the coordinates that are allocated to the volume dataset.

According to a variant of the invention, the coordinates of the images of the marks in the image dataset are determined by filtering the image dataset. A filter that is matched to the marks is utilized for the filtering according to a preferred variant of the invention. For the matched filter, a pattern image (template) of how each image of the marks would be represented in this flat image is computed from the known dimensions of the marks on the scale of the unrolled image of the segmented body surface. Basically, known methods of template matching can now be applied for localizing existing images of the marks in the area, such as the methods known from German PS 44 35 796 or from "Digital Picture Processing" (Rosenfeld & Kak, AP 1982, pp. 37-49).

According to a further variant of the invention, the filtering can be a filtering in the sense of mathematical correlation. This filtering possesses the characteristic that exactly one location of the image of each mark emerges as the local maximum. These local maxima are searched in the 2D image data. This correlation based maximum search is the equivalent of the determination of the local minimal square error sum as provided in a further embodiment of the invention.

The automatic registering of the subject can then even be completed by the mark recognition on the subject also being performed automatically, for instance by automatic identification of the marks directly at the beginning of the intervention, such as in an optical field, an electromagnetic field, or a sound field. Industrial image processing techniques such as the 2D data matrix code as described in the example of ECC200 in ISO/IEC 16022 can be applied as the mark format. The marks are distinguished from one another by a specific marking content such as 2D matrix code. Another embodiment uses LEDs with light of a defined and distinct wavelength or color, or LEDs that are pulsed at distinct times or with different frequencies and optically detected and localized.

The object of the invention also is achieved by a medical device with a data processing device that is provided for storing a volume dataset and with a navigation system, wherein the volume dataset is recorded with a first imaging medical device and represents an image of at least part of a subject on whose surface several marks are arranged, and images of the marks, and wherein a relationship between the coordinates of the volume dataset and the coordinates of the subject is produced in the form of a coordinate transformation with the navigation system during a registration, and wherein the determination of the coordinates of the images of the marks in the volume dataset for the registration is undertaken according to the inventive method. With the inventive medical device, the registration can be accomplished relatively quickly.

According to a variant of the invention, the marks for the registration are identified with a position sensor of the navigation system. According to an embodiment of the invention, the position sensor is a magnetic sensor, and according to a different embodiment, it is an optical mark that is localized by a camera.

According to another variant of the invention, the medical device includes a second imaging medical device for recording images of the living being, so that the images that are recorded with the second imaging medical device can be faded into an image that is allocated to the volume dataset.

DESCRIPTION OF THE DRAWINGS

FIG. 2 is a three-dimensional image of the stomach area of a patient in the form of a volume dataset formed by several slice images.

FIG. 4 is a slice image of the volume dataset represented in FIG. 2.

FIG. 5 shows image information of the slice image represented in FIG. 4 subsequent to its transformation to polar coordinates

Figure 9:
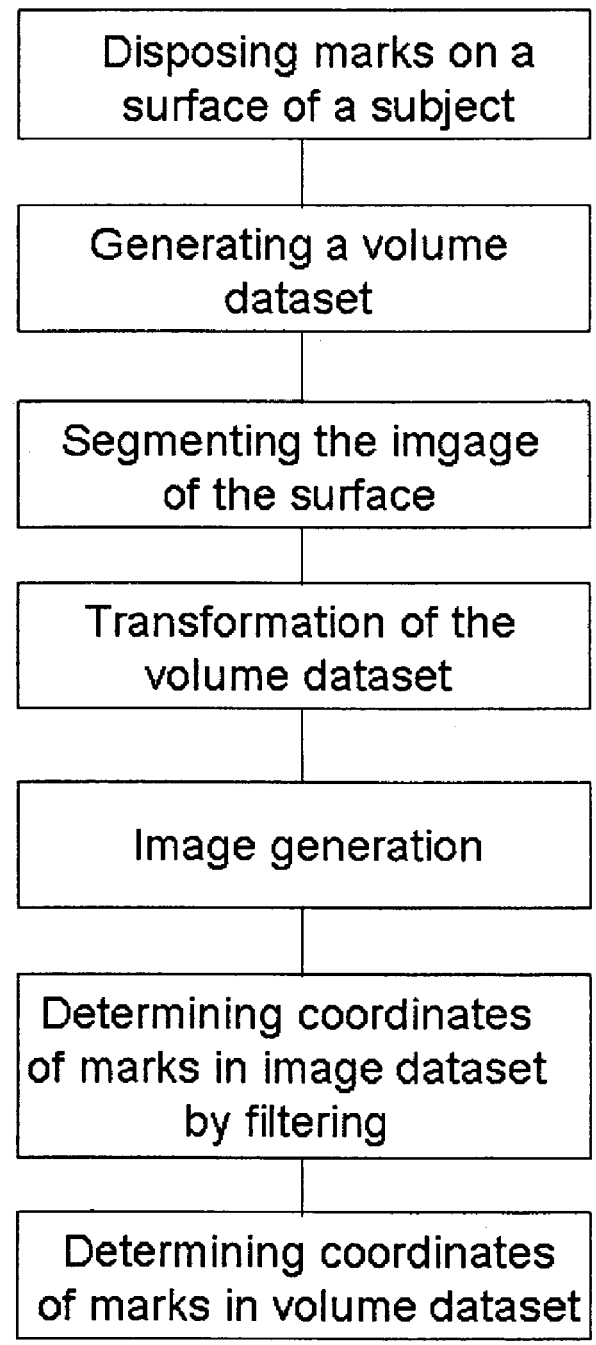
FIG. 9 is a flow chart illustrating an embodiment of the invention.

The steps described in detail below are summarized in the flow chart shown in FIG. 9.

DESCRIPTION OF THE PREFERRED EMBODIMENTS

Figure 1:
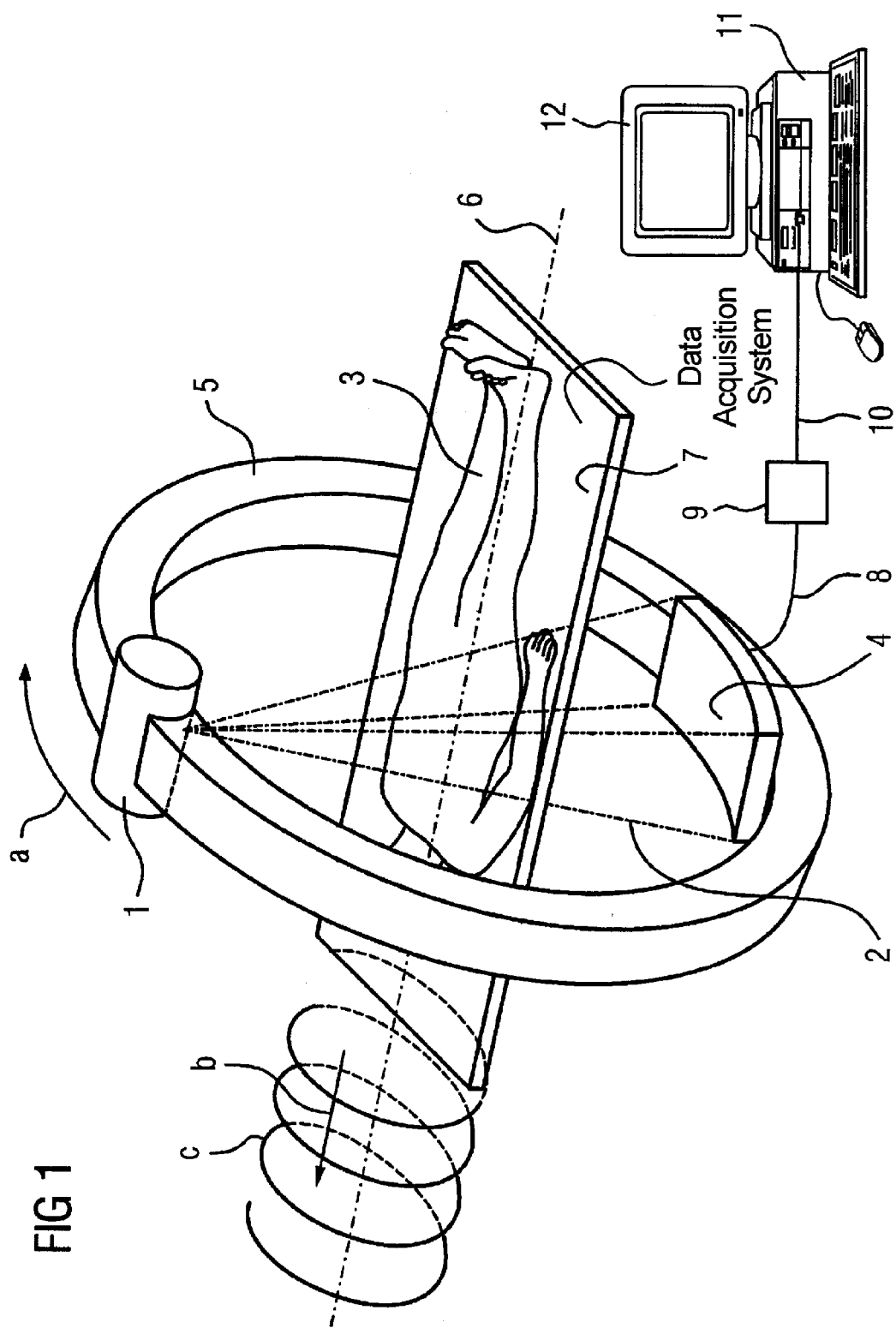
FIG. 1 is a computed tomography apparatus operable in accordance with the invention.

FIG. 1 is a schematic representation of a computed tomography apparatus with an X-ray source 1 which emit a pyramidal X-ray beam 2, the peripheral rays of which are represented as dotted lines in FIG. 1, which passes through an examination subject, for instance a patient 3, and strikes a radiation detector 4. In the exemplary embodiment. there are four marks 13 disposed on the body of the patient, which are imaged in an image dataset that is recorded with the computed tomography apparatus. The marks 13 are small, flat aluminum disks containing holes in this instance. This X-ray source 1 and the X-ray detector 4 are disposed facing one another on opposite sides of an annular gantry 5. The gantry 5 is supported at a bearing device that is not shown in FIG. 1 such that it pivots relative to a system axis 6 that extends through the midpoint of the annular gantry 5 (arrow a).

In the present exemplary embodiment, the patient 3 lies on a table 7 that is transparent to X-rays, which is supported by a bearing device that is not shown in FIG. 1 so that it can be displaced along the system axis 6 (arrow b).

The X-ray source 1 and the X-ray detector 4 form a measuring system which is rotatable relative to the system axis 6 and displaceable along the system axis 6 relative to the patient 3, so that the patient can be irradiated at different projection angles and different positions relative to the system axis 6. From the generated output signals of the radiation detector 4, a data acquisition system 9 forms measurement values, which are fed to a computer 11, which computes, by methods known those skilled in the art, an image of the patient 3 that can be reproduced on a monitor 12 that is connected to the computer 11. In the exemplary embodiment, the data acquisition system 9 is connected to the radiation detector 4 by an electrical line 8, which terminates in a wiper ring system or has a wireless transmission path to obtain signals from the radiation detector 4, and ft is connected to the computer 11 by an electrical line 10.

The computed tomography apparatus represented in FIG. 1 can be utilized for sequential scanning and spiral scanning.

In sequential scanning, the patient 3 is scanned slice by slice. The X-ray source 1 and the X-ray detector 4 are rotated about the patient 3 relative to the system axis 6, and the measuring system, which is formed by the X-ray source 1 and the X-ray detector 4, captures a number of projections in order to scan a two-dimensional slice of the patient 3. From the measurement values so acquired, a slice image representing the scanned slice is reconstructed. Between the scanning of consecutive slices, the patient 3 is moved along the system axis 6. This process is repeated until all relevant slices are picked up.

During a spiral scan, the measuring system comprising the X-ray source 1 and the X-ray detector 4 rotates relative to the system axis 6, and the table 7 moves continuously in the direction of arrow b; that is, the measuring system formed by the X-ray source 1 and the X-ray detector 4 continuously moves on a spiral path c relative to the patient 3 until the region of interest of the patient 3 is completely covered. A volume dataset is thereby generated, this being done according to the customary DICOM standard in the present embodiment.

In the exemplary embodiment, a volume dataset of the stomach area of the patient 3 consisting of several consecutive slice images is generated with the computed tomography apparatus shown in FIG. 1. The volume dataset that is represented schematically in FIG. 2 contains approximately 250 CT slices (slice images) of the matrix 512×512. FIG. 2 shows seven slice images as an example, which are indicated by reference characters 21 to 27. The volume dataset 20 also contains images 20 of the marks 13 on the body of the patient 3. The volume dataset is stored in the computer 11.

Figure 3:
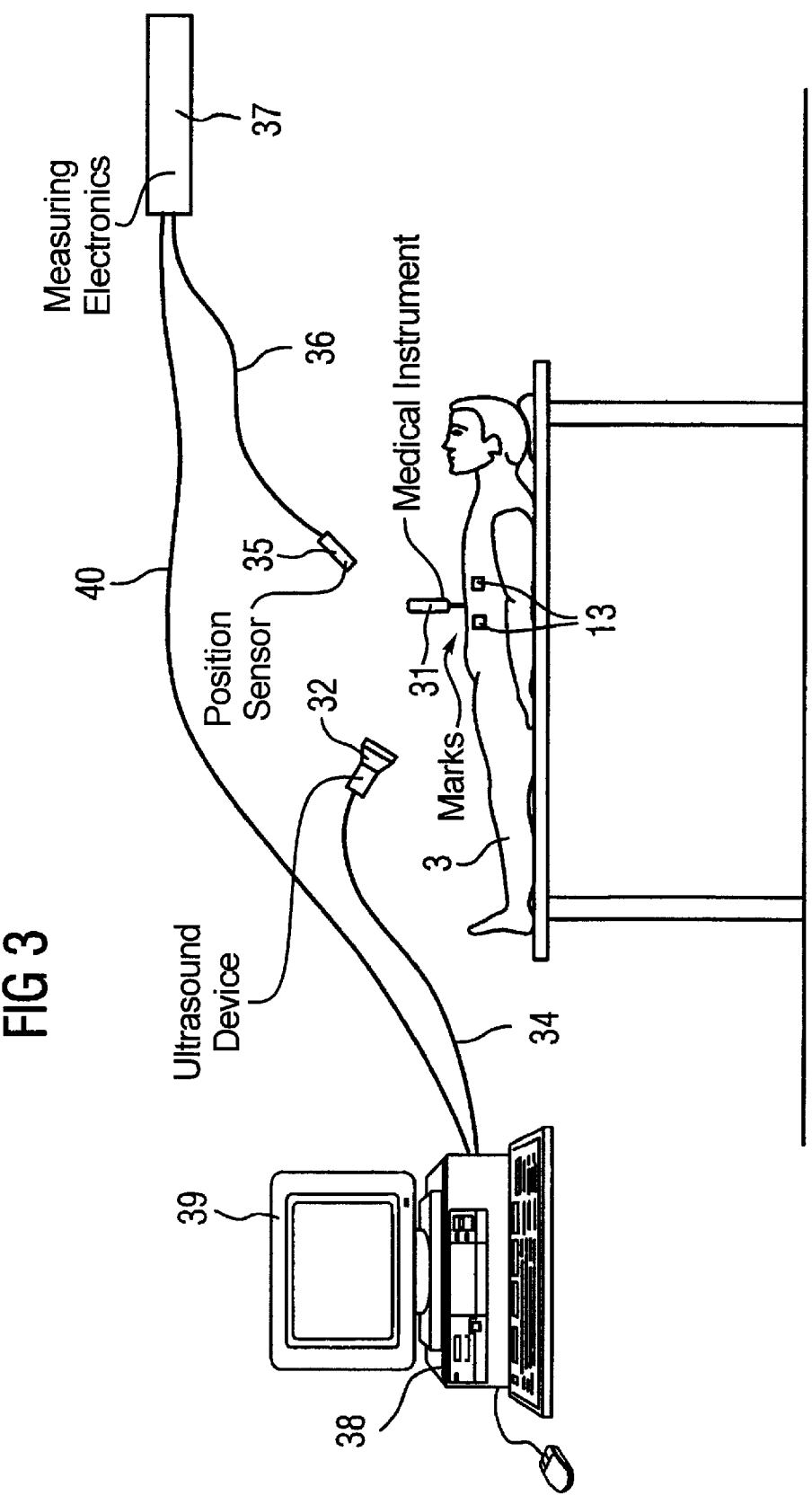
FIG. 3 illustrates a medical workspace.

After the volume dataset of the patient 3 that is represented in FIG. 2 has been generated, the patient 3 is moved to a medical workspace shown in FIG. 3, where the patient is to be treated in a minimally invasive fashion, by a physician (not shown) using a medical instrument 31, for instance a laparoscope, endoscope, or catheter. During the treatment, the marks 13 remain on the body of the patient 3. During the intervention with the medical instrument 31, the image of the medical instrument 31 should be faded into the volume dataset that is produced by the computed tomography apparatus. In the exemplary embodiment, there is also an ultrasound device 32 available to the physician with which the physician can monitor the intervention if necessary. In the exemplary embodiment the image data that are picked up by the ultrasound device 32 are overlapped by the volume dataset that was picked up with the computed tomography apparatus.

To that end, the medical workspace includes a computer 38 to which the volume dataset that is picked up with the computed tomography apparatus is imported for the intervention. The ultrasound device 32 is connected to the computer 38 by an electrical line 34. For importing the volume dataset, in the exemplary embodiment the computer 38 is connected to a hospital information system, (not shown) to which the computer 11 of the computed tomography apparatus device is also is connected, by means not shown in FIG. 3, so that the volume dataset can be transferred from the computer 11 to the computer 38 via the hospital information system.

With a monitor 39 that is connected to the computer 38, the physician can view and process an image that is allocated to the volume dataset.

For fading the image of the medical instrument 31 into the image that is allocated to the volume dataset, i.e. for overlapping the volume dataset onto the image data that are picked up with the ultrasound device 32, the medical workspace shown in FIG. 3 has a navigation system, for instance a system that is known from German OS 199 51 502, which has a magnetic field generator, which contains control and measuring electronics 37, and a position sensor 35. The magnetic field generator having control and measuring electronics 37 forms a navigation computer of the navigation system, and is connected to the position sensor 35 by an electrical line 36. The navigation computer evaluates the signals that are picked up by the sensor 35 and calculates the spatial position and orientation of the position sensor 35 therefrom.

During the medical intervention with the medical instrument 31, the position sensor 35 is placed on the medical instrument 31, so that the navigation computer of the magnetic field generator having control and measuring electronics 37 can determine the current position and orientation of the medical instrument 31 based on the acquired signals.

During the examination by means of the ultrasound device 32, the position sensor 35 or a second such sensor is placed on the ultrasound device 32, so that the navigation computer of the magnetic field generator containing control and measuring electronics 37 can compute the current position and orientation of the ultrasound device 32 based on the acquired camera images.

The navigation computer of the magnetic field generator containing control and measuring electronics 37 is connected to the computer 38 by an electrical line 40 and supplies the data about the current positions of the medical instrument 31 or ultrasound device 32 to the computer 38 so that the computer 38 can determine the precise position and orientation of the medical instrument 31 or ultrasound device 32 relative to the situs of operation. In this manner, an image of the medical instrument 31 can be faded into the image that is allocated to the volume dataset and displayed on the monitor 39, or an image that is picked up by the ultrasound device 32 can be overlapped by the image that is allocated to the volume dataset.

A registration as described in the introduction, in which a relation is created between the coordinates of the coordinate system that is allocated to the volume dataset and the coordinate system of the navigation system, is still needed for the overlapping or fading.

For the registration, which is known to those skilled in the art, the marks 13 are tapped with the position sensor 35 of the navigation system, whereby the positions of the individual marks 13, and thus their coordinates in the coordinate system of the navigation system, are determined. With the tapping of one of the marks 13, the corresponding image of the mark in the volume dataset is selected. Once all mark positions have been determined, each coordinate of the marks 13 in the coordinate system of the navigation system is automatically allocated to the corresponding coordinates of the images of marks 13 in the volume dataset.

The manual moving to the mark positions can be automated by providing the marks 13 with reflectors and gluing on square fields containing data matrix code that are glued on, for example.

As mentioned above, the coordinates of the images of the marks 13 in the volume dataset are needed for registration. In the exemplary embodiment, these are determined by a computer program that runs on the computer 38, which executes the steps described below.

First, the computer program that runs on the computer 38 segments the three-dimensional image of the patient 3 in the volume dataset in order to determine the body surface. For the segmenting according to the exemplary embodiment, each slice image 21 to 27 of the volume dataset is first transformed to polar coordinates $(r,\phi)$ relative to a line G through the three-dimensional image of the stomach region of the patient 3 in a first pass. The line G is oriented substantially perpendicular to the individual slice images 21 to 27. In the case of the present exemplifying embodiment, the line G extends through the center of the volume dataset and corresponds to the z-axis of the coordinate system that defines the volume dataset.

In the exemplary embodiment, each slice image 21 to 27, of which the slice image 22 is represented in FIG. 4, is described with Cartesian coordinates (x,y). Next, the image information of each slice image 21 to 27 is rearranged radially, being transformed to polar coordinates $(r,\phi)$ relative to the line G, i.e. relative to the respective point of intersection between the line G and the corresponding slice image. As an example, the point of intersection S between the line G and the slice image 22 is represented in FIG. 4.

The result of such a coordinate transformation is represented in FIG. 5. With the transformation to polar coordinates $(r,\phi)$, the image of the body surface of the patient 3 is also transformed, being represented as a closed contour in each transformed axial slice (slice image). FIG. 5 represents an example of a contour 51 that is allocated to the image of the body surface of the patient 3 for the slice image 22 subsequent to its transformation to polar coordinates $(r,\phi)$.

Figure 10:
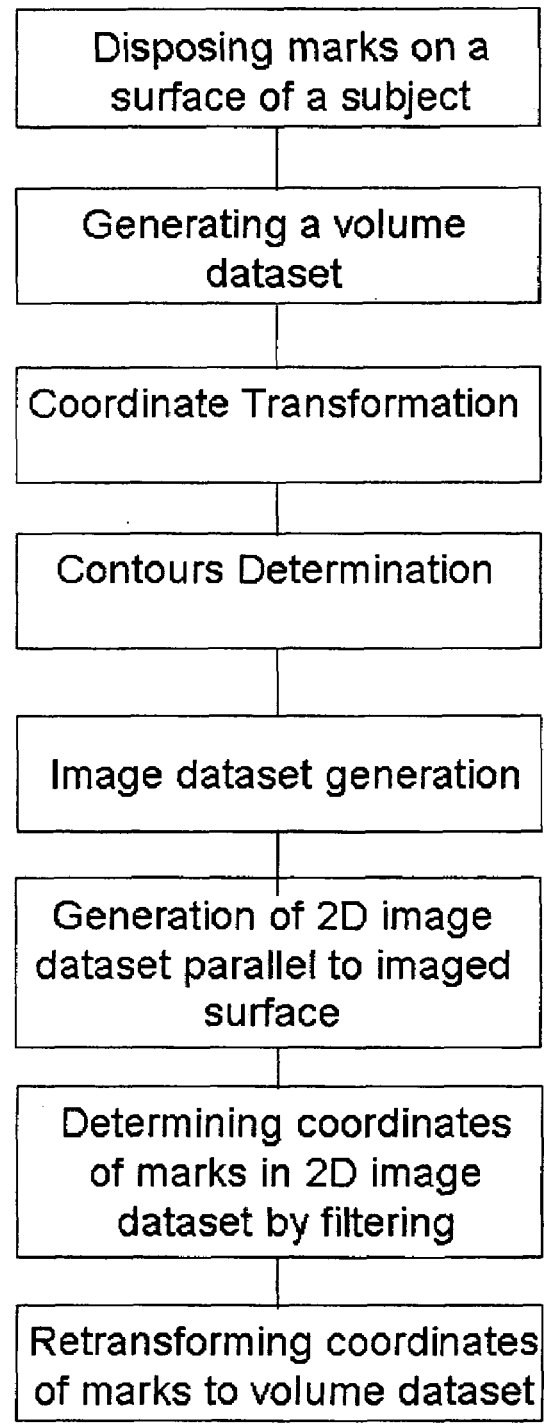
FIG. 10 is a flow chart illustrating a further embodiment of the invention.

A flow chart illustrating the basic steps of the above-described embodiment employing contour determination is shown in FIG. 10.

The result of the transformation to polar coordinates $(r,\phi)$ is a radial brightness profile $r(\phi)$ plotted linearly over $\phi$. In this rectangular matrix (derivative image matrix), a filtering is performed, which highlights the contours that are allocated to the body surface, such as the contour 51 represented in FIG. 5. The filter responses replace the brightness values in the derivative image matrix. Next is the search for the optimal path in this image matrix from top (r coordinate for $\phi$=0o) to bottom (r coordinate for $\phi$=360o) at the substantially identical start point/end point (a margin condition being that the r coordinate for $\phi$=0o should equal the r coordinate for $\phi$=360o). In the case of the present exemplifying embodiment, this occurs by means of dynamic optimization, such as described in Dynamic programming and stochastic control processes (R. Bellmann, Information and Control 1(3), September 1958: 228-39). The optimal path represents the radial vectors to the pixels that are allocated to the body surface. In a further step, the whole contour ensemble that is determined from the individual contours of the slice images 21 to 27 is checked in relation to the individual contours across all slice images 21 to 27. This contributes particularly to the suppression of errors (outliers) and to reliability of the segmenting of the whole image of the body surface of the patient 3. At the probable points of error, re-segmenting is performed based on the contours found thus far in the individual slice images 21 to 27, with subsequent checking of the 3D context. The image of the patient 3 in the volume dataset is thus segmented with the result of the (x,y,z) coordinates of the whole body surface.

Figure 6:
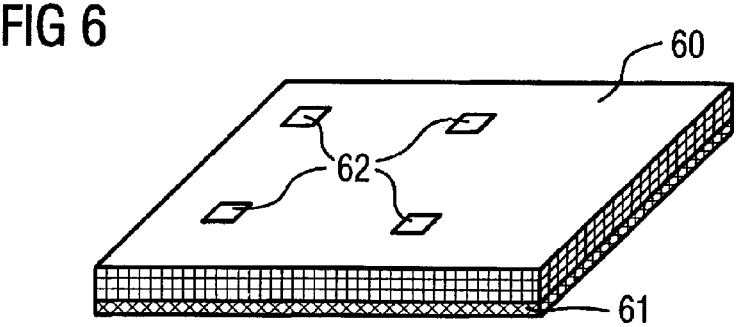
FIG. 6 is an image dataset representing the image of the body surface subsequent to its transformation into a plane and an image of a few slices that adjoin the body surface.

In the exemplary embodiment, this is followed by a re-extraction at a right angle to the image of the segmented body surface in the volume dataset. Whereas, in the transformation to polar coordinates $(r,\phi)$, brightness profiles were computed at a right angle to all points of a circle (surface idealized as start value: in slices, a circle; in 3D blocks, a cylinder) and mapped as a rectangular matrix, in the re-extraction profiles are obtained at each pixel of the body surface at a right angle to the image of the segmented body surface (body surface contour) at this point. This re-extraction is remapped as a rectangular matrix. A line from left to right therein, for instance the centerline, corresponds to the pixels of the image of the body surface of a slice, for instance the center slice. For example, above this in FIG. 6 are the CT measurement values near the body surface on the outside, i.e. the voxel values that are allocated to the applied marks 20. With the overall re-extraction, the volume dataset is so transformed that the segmented image of the body surface of the patient 3 is represented in combination with parallel adjoining thin slices over one plane.

As a result, an image dataset 60 emerges as shown in FIG. 6, which has the structure of a thin voxel cuboid. In FIG. 6 the image of the body surface of the patient 3 after transformation into the plane is referenced 61. The three voxel slices shown as an example above it adjoin the body surface on the outside and represent the images of the marks 13, which are referenced 62. The four slices shown as an example in FIG. 6 can be linked with a mathematical operator over all four columns, for instance by average value formation (with noise suppression) or the selection of the maximum of the four CT values, as in a maximum intensity projection (MIP). That way a dataset is not simply generated according to the entity (as in FIG. 6 with four planar slices on top of one another), but rather a two-dimensional dataset is precisely generated.

Figure 7:
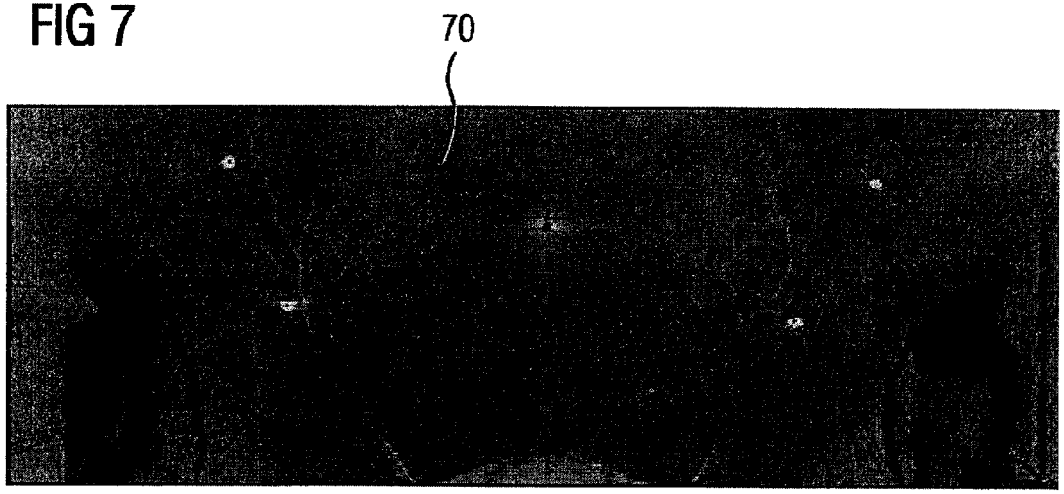
FIG. 7 is the image that is allocated to the image dataset represented in FIG. 6, wherein the imaged body surface and adjoining imaged slices are combined.

FIG. 7 shows an image 70, which is allocated to the image dataset represented in FIG. 6, the imaged body surface being combined with adjoining imaged slices.

Owing to the relatively low Hounsfield values of the body surface aluminum marks like marks 13 in the exemplary embodiment contrast relatively well in the image 70 that is allocated to the image dataset 60 which is represented in FIG. 7 in plan view, far better than such marks stand out in a volume dataset (FIG. 2).

Next, the computer program that runs on the computer 38 determines the coordinates of the images 62 of the marks 13 in the image dataset 60. To that end, in the case of the present exemplifying embodiment a template is created from the known measurements of the marks 13 on the imaging scale of the images 62 in the image dataset 60.

Figure 8:
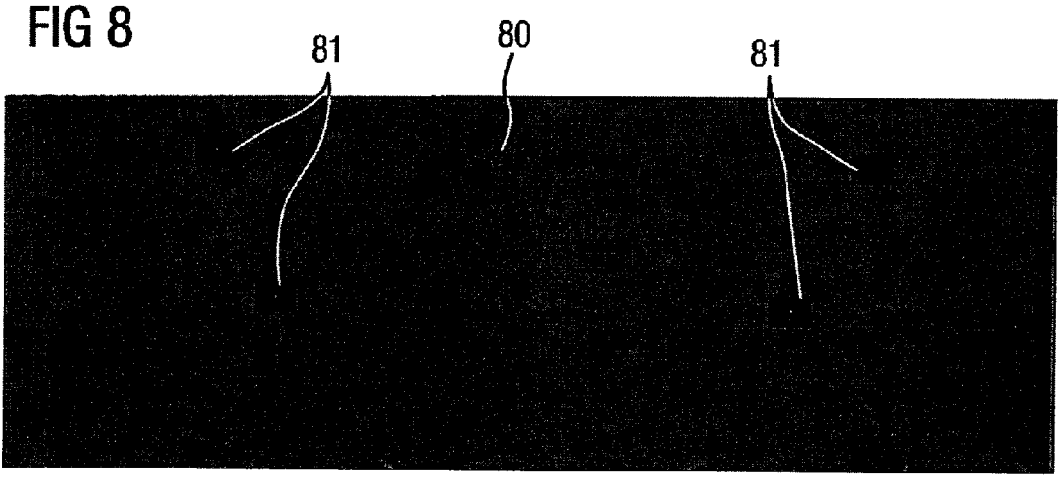
FIG. 8 is an image that is allocated to an image dataset according to FIG. 6 that has been filtered by a matched filter, in which the four white points represent unambiguous global maxima that are laid against a black background so that they are recognizable as individual points.

For the determining of the coordinates of the images 62 the image dataset 60 is convoluted with this template; to be precise, a correlation calculation of the image data of the image dataset 60 is performed with the pixel values of the template as the filter coefficients. The template thus is continuously shifted across the entire image dataset 60 and calculated with the overlapped image region, respectively. There emerges an optimal filter response according to the criterion of the smallest error square sum. The smallest error square sum technique is described in "Digital Picture Processing" (Rosenfeld & Kak, AP, 1982: 37-49). Because the template was computed from the dimensions of the marks 38 being searched for, this calculation amounts to an embodiment of what is known as a matched filter. The image 80 that is filtered this way is shown in FIG. 8 (filter response). The images of the positions of the marks 13 after the filtering are referenced 81.

A particularly notable advantage of the filtering in the case of the exemplary embodiment is that an unambiguous maximum emerges in the middle of the imaged positions of the marks 13 in the filtered image 80. The coordinates of the images 62 and 81 of marks 13 emerge directly as the positions of the filter maxima in the case of the present exemplifying embodiment.

Lastly, the coordinates of the images 62 and 81 of marks 13 in the coordinate system of the image dataset 60 are transformed back into the coordinates of the volume dataset. This transformation corresponds to the inverse of the transformation that transforms the original volume dataset into the image dataset of FIG. 6, or more precisely, into the image 61 of the body surface.

In the exemplary embodiment, the volume dataset is produced with a computed tomography apparatus. In the inventive method and the inventive medical device, the volume dataset alternatively can be produced with some other imaging device.

The volume dataset need not take the form of several consecutive computed tomography slice images.

The navigation system (35-37) need not necessarily be a magnetic navigation system. In particular, an optical or electrical or sound-based navigation system can be used.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining coordinates of images of marks in a volume dataset comprised of a plurality of consecutive computed tomography slice images of a subject in which image data in each slice image are described with Cartesian coordinates, and wherein the marks are disposed on a surface of the subject, and wherein the volume dataset represents images of the marks and an image of at least a part of the subject having a surface on which the marks are disposed, said method comprising the steps of:

performing a coordinate transformation for each slice image from Cartesian coordinates to polar coordinates relative to a line extending through the image of the subject, said line being oriented substantially perpendicularly to the slice images, thereby obtaining transformed sliced images;

determining contours in each of said transformed slice images allocated to the surface of the subject in that transformed slice image;

generating an image dataset substantially comprising pixels of the image of the surface after transformation into a plane and pixels of the images of the marks;

generating a two-dimensional image dataset by re-extracting image data representing the images of the marks in a region parallel to the imaged surface;

determining coordinates of the images of the marks in the two-dimensional image dataset; and re-transforming the coordinates of the images of the marks back into the coordinates allocated to the volume dataset.

2. A method as claimed in claim 1 comprising determining the coordinates of the images of the marks in the image dataset and in the two-dimensional image dataset by filtering said image dataset.

3. A method as claimed in claim 2 comprising filtering said image dataset with a filter matched to said marks.

4. A method as claimed in claim 2 comprising filtering said image dataset according to the minimum square error sum.

5. A method as claimed in claim 2 comprising filtering said image dataset to cause at least one location of the image of each mark to emerge as a local maximum.

6. A computed tomography system comprising:

a computed tomography imaging device for obtaining a volume dataset of a subject representing a plurality of consecutive computed tomography slice images of the subject, each slice image comprising image data described with Cartesian coordinates, and wherein marks are disposed on a surface of the subject and the volume dataset represents images of the marks and an image of at least a part of the subject having the surface on which the marks are disposed;

a data processing system supplied with said volume dataset, said data processing system storing said volume dataset;

a navigation system for relating coordinates of the volume datasets to coordinates of the subject by a coordinate transformation during a registration; and said navigation system performing a coordinate transformation for each slice image from said Cartesian coordinates to polar coordinates relative to a line extending through the image of the subject, said line being oriented substantially perpendicularly to the slice images, thereby obtaining transformed sliced images, determining contours in each of said transformed slice images allocated to the surface of the subject in that transformed slice image, generating an image dataset substantially comprising pixels of the image of the surface after transformation into a plane and pixels of the images of the marks, generating a two-dimensional image dataset by re-extracting image data representing the images of the marks in a region parallel to the imaged surface, determining coordinates of the images of the marks in the two-dimensional image dataset, and re-transforming the coordinates of the images of the marks back into the coordinates allocated to the volume dataset.

7. A computed tomography system as claimed in claim 6 comprising a filter for filtering the image dataset to determine the coordinates of the marks in the image dataset and in the two-dimensional image dataset.

8. A computed tomography system as claimed in claim 7 wherein said filter is matched to the marks.

9. A computed tomography system as claimed in claim 7 wherein said filtering filters according to the minimum square error sum.

10. A computed tomography system as claimed in claim 7 wherein said filter causes at least one location of the image of each mark to emerge as a local maximum.

11. A computed tomography system as claimed in claim 6 wherein said navigation system includes a position sensor for identifying the marks for the registration.

12. A computed tomography system as claimed in claim 11 wherein said marks are optically detectable and wherein said position sensor is an optical detector.

13. A computed tomography system as claimed in claim 6 further comprising a separate medical imaging device for obtaining images of the subject and for fading images obtained with the medical imaging device into an image allocated to the volume dataset.

* * * * *